(12) United States Patent
Bazargan

(10) Patent No.: US 10,552,580 B2
(45) Date of Patent: Feb. 4, 2020

(54) INFUSION SYSTEM CONSUMABLES AND RELATED CALIBRATION METHODS

(71) Applicant: MEDTRONIC MINIMED, INC., Northridge, CA (US)

(72) Inventor: Afshin Bazargan, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 194 days.

(21) Appl. No.: 15/427,019

(22) Filed: Feb. 7, 2017

(65) Prior Publication Data

US 2018/0225423 A1    Aug. 9, 2018

(51) Int. Cl.
*A61M 5/14* (2006.01)
*G06F 19/00* (2018.01)
*A61M 5/142* (2006.01)
*A61M 5/172* (2006.01)
*F04B 19/22* (2006.01)
(Continued)

(52) U.S. Cl.
CPC ..... *G06F 19/3468* (2013.01); *A61M 5/14216* (2013.01); *A61M 5/14228* (2013.01); *A61M 5/1723* (2013.01); *F04B 19/22* (2013.01); *F04B 23/02* (2013.01); *F04B 43/12* (2013.01); *F04B 51/00* (2013.01); *G16H 40/63* (2018.01); *A61M 2205/3334* (2013.01); *A61M 2205/3584* (2013.01); *A61M 2205/502* (2013.01); *A61M 2205/52* (2013.01); *A61M 2205/6072* (2013.01);
(Continued)

(58) Field of Classification Search
CPC .. A61M 2205/3334; A61M 2205/3584; A61M 2205/502; A61M 2205/52; A61M 2205/6072; A61M 2205/70; A61M 2207/00; A61M 2230/201; A61M 5/14216; A61M 5/14228; A61M 5/1723; F04B 19/22; F04B 2205/05; F04B 2205/09; F04B 23/02; F04B 43/12; F04B 43/1253; F04B 43/1269; F04B 51/00; F04B 9/045; G06F 19/3468; G16H 40/63
See application file for complete search history.

(56) References Cited

U.S. PATENT DOCUMENTS 3,631,847 A    1/1972    Hobbs, II
4,212,738 A    7/1980    Henne
(Continued)

FOREIGN PATENT DOCUMENTS

DE    4329229    3/1995
EP    0319268    11/1988
(Continued)

OTHER PUBLICATIONS

PCT Search Report (PCT/US02/03299), dated Oct. 31, 2002, Medtronic Minimed, Inc.
(Continued)

*Primary Examiner* — Imani N Hayman
(74) *Attorney, Agent, or Firm* — Lorenz & Kopf, LLP

(57) ABSTRACT

Infusion systems including infusion devices and consumables and related operating methods are provided. An exemplary consumable component includes a housing, a reservoir contained within the housing, a pumping mechanism for dispensing a fluid from the reservoir, and a readable element associated with the housing. The readable element maintains calibration data characterizing a relationship between delivery of the fluid and actuation of the pumping mechanism.

9 Claims, 7 Drawing Sheets

(51) Int. Cl.
*F04B 23/02* (2006.01)
*F04B 43/12* (2006.01)
*F04B 51/00* (2006.01)
*G16H 40/63* (2018.01)

(52) U.S. Cl.
CPC ..... *A61M 2205/70* (2013.01); *A61M 2207/00* (2013.01); *A61M 2230/201* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |

(56) References Cited

U.S. PATENT DOCUMENTS

| | | |
|---|---|---|
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2005/0192561 A1 | 9/2005 | Mernoe |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2012/0030610 A1 | 2/2012 | DiPerna et al. |
| 2015/0306304 A1 | 10/2015 | Schabbach et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting A Primer for Insulin Pump Users to Zero in on Good Control. MiniMed Inc.

Marcus A O et al. (1996). insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

(56) References Cited

OTHER PUBLICATIONS

Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. pp. 66-78.
Disetronic My Choice™ D-TRON™ Insulin Pump Reference Manual. (Actual date of publication/release unknown, but Applicant has been aware of the cited document as of Nov. 30, 2007).
Disetronic H-TRON® plus Quick Start Manual. (Actual date of publication/release unknown, but Applicant has been aware of the cited document as of Nov. 30, 2007).
Disetronic My Choice H-TRONplus Insulin Pump Reference Manual. (Actual date of publication/release unknown, but Applicant has been aware of the cited document as of Nov. 30, 2007).
Disetronic H-Tron® plus Reference Manual. (Actual date of publication/release unknown, but Applicant has been aware of the cited document as of Nov. 30, 2007).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: hltp://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International; 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.

Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analylica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263. (Actual date of publication/release unknown, but Applicant has been aware of the cited document as of Nov. 30, 2007).
Gregg, Brian A., et al., "Redox Polymer Films Containing Enzymes. 1. A Redox-Conducting Epoxy Cement: Synthesis, Characterization, and Electrocalalytic. Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzyrnatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Navel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.

(56) References Cited

OTHER PUBLICATIONS

Nishida, Kenro, et al., "Clinical applications of teh wearable artificial endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, el al., "Closed-Loop Glycemic Control with a Wearable Artificial Endocrine Pancreas—Variations in Daily insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-134.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators. vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosertsors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

INFUSION SYSTEM CONSUMABLES AND RELATED CALIBRATION METHODS

CROSS-REFERENCE TO RELATED APPLICATIONS

The subject matter described here is related to the subject matter described in U.S. patent application Ser. No. 15/427,015, filed concurrently herewith.

TECHNICAL FIELD

Embodiments of the subject matter described herein relate generally to medical devices, and more particularly, embodiments of the subject matter relate to operation of a fluid infusion device using pre-calibrated consumables.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a corresponding delivery of medication from a reservoir to the body of a user via a fluid path created between the reservoir and the body of a user. Use of infusion pump therapy has been increasing, especially for delivering insulin for diabetics. Continuous insulin infusion provides greater control of a patient with diabetes glucose levels, and hence, control schemes are being developed that allow insulin infusion pumps to monitor and regulate a user's blood glucose level in a substantially continuous and autonomous manner.

In practice, it is desirable to accurately monitor and control the volume of fluid delivered to the user. However, designing a flow meter or similar component than can accurately cover the entire range of incremental amounts of fluid that may be delivered in a single delivery operation may be costly or problematic once durability, reliability and other constraints are considered. Moreover, the design of the flow meter may be further complicated by the form factor of the infusion device or other packaging constraints. Additionally, depending on the type of pump or fluid delivery technology employed, the flow meter may contact the fluid being infused, which, in turn, may require periodic replacement or disposal of the flow meter or some of its components. Accordingly, there is a need to accurately monitor and control the volume of fluid delivered without compromising device form factor or incorporating a potentially costly flow meter or similar component that satisfies the various requirements that may be imposed.

BRIEF SUMMARY

Infusion systems, infusion devices, consumables, and related operating methods are provided. An embodiment of a method of operating an infusion device to deliver fluid capable of influencing a physiological condition to a body of a user is provided. The method involves obtaining, by a control module of the infusion device via an interface of the infusion device, calibration data associated with a consumable coupled to the infusion device, determining, by the control module, a delivery command for delivering the fluid to the body of the user based at least in part on the calibration data, and operating, by the control module, a pumping mechanism to deliver the fluid from the consumable in accordance with the delivery command. Thus, the amount or rate of fluid delivered may be influenced by the calibration data.

In another embodiment, an apparatus for an infusion device is provided. The infusion device includes a housing including a portion for receiving a consumable, an interface proximate the portion of the housing to obtain configuration data from the consumable, an actuation arrangement contained within the housing and configured to actuate a pumping mechanism operable to dispense a fluid from the consumable, and a control module coupled to the interface and the actuation arrangement to determine a delivery command based at least in part on the calibration data and operate the actuation arrangement in accordance with the delivery command.

In another embodiment, an infusion system is provided. The system includes a consumable including a pumping mechanism for dispensing a fluid and a readable element maintaining calibration data characterizing a relationship between delivery of the fluid and actuation of the pumping mechanism. The system also includes an infusion device including an interface to obtain the calibration data from the readable element, an actuation arrangement configured to actuate the pumping mechanism, and a control module coupled to the interface and the actuation arrangement to determine a delivery command based at least in part on the calibration data and operate the actuation arrangement in accordance with the delivery command.

In another embodiment, an apparatus for a consumable component is provided. The consumable component includes a housing, a reservoir contained within the housing, a pumping mechanism for dispensing a fluid from the reservoir, and a readable element associated with the housing, the readable element maintaining calibration data characterizing a relationship between delivery of the fluid and actuation of the pumping mechanism.

A method of manufacturing a consumable component including a pumping mechanism is also provided. The method involves actuating, by a control module, the pumping mechanism of the consumable component by a reference amount, obtaining, by the control module from a sensing arrangement, a measured response to the reference amount, determining, by the control module, calibration data associated with the consumable based on the relationship between the measured response and the pumping mechanism, and writing, by the control module, the calibration data to a readable element associated with the consumable.

In yet another embodiment, a system is provided that includes a consumable and an infusion device. The consumable includes a housing containing a reservoir and a pumping mechanism in fluid communication with the reservoir to dispense a fluid from the reservoir, and a readable element associated with the housing. The readable element maintains calibration data characterizing a relationship between delivery of the fluid and actuation of the pumping mechanism. The infusion device is configured to receive the housing and includes an interface to obtain the calibration data from the readable element, wherein the calibration data influences operation of the pumping mechanism by the infusion device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
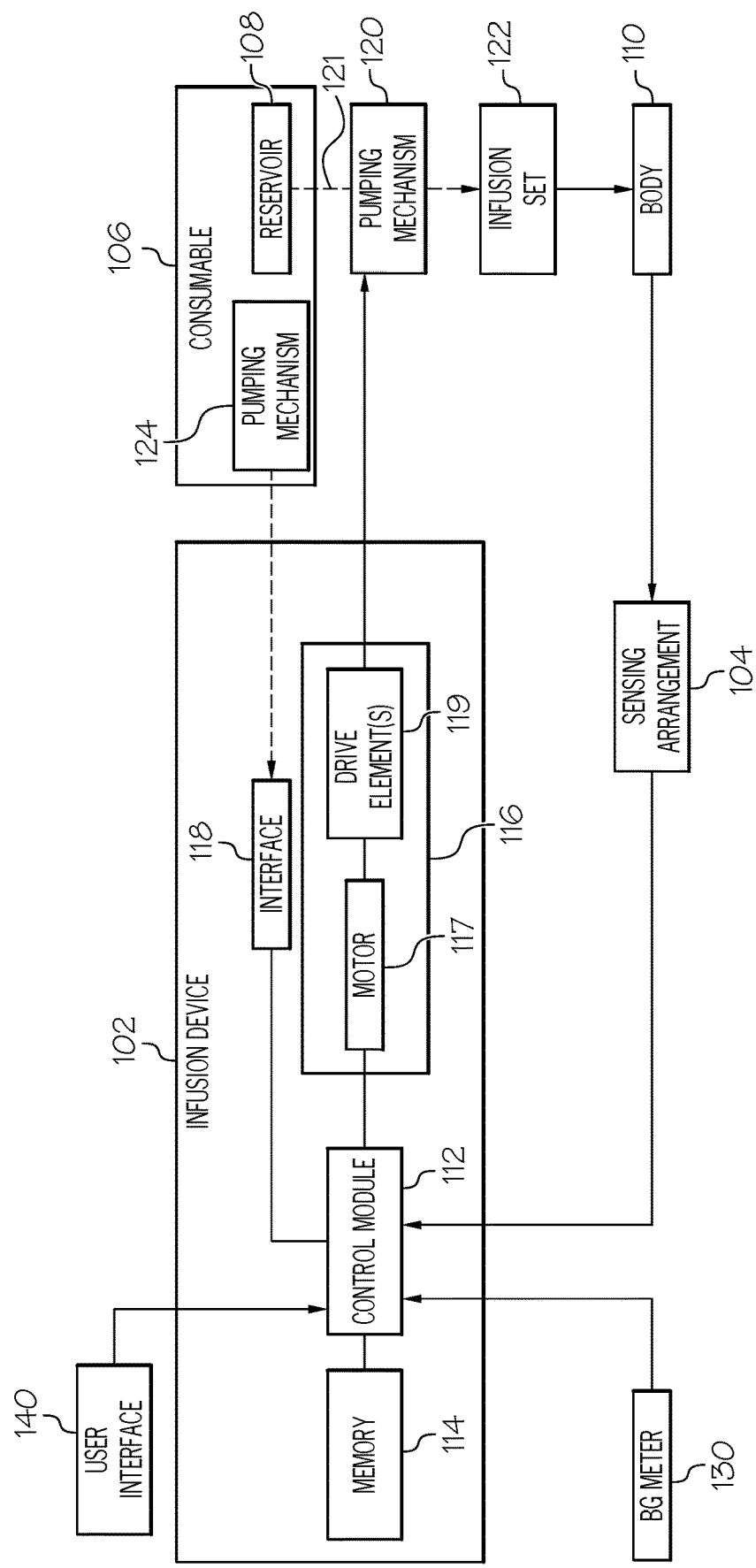
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to infusion systems including a fluid infusion device having an actuation arrangement that is operable to actuate a mechanism that facilitates delivering a dosage of fluid, such as insulin, from a reservoir to a body of a patient (or user) via an infusion arrangement, such as a needle, cannula, infusion set, or the like. Dosage (or delivery) commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below, in exemplary embodiments described herein, the fluid infusion device receives a consumable that is disposed of, changed or otherwise replaced periodically. As used herein, a consumable should be understood as referring to any element or component that is capable of being detachably engaged with, inserted into, or coupled to the fluid infusion device to support delivery of fluid. In exemplary embodiments, the consumable includes a fluid reservoir and is disposed of or replaced upon depletion of the fluid reservoir.

In exemplary embodiments, the consumable includes a readable element or similar feature that stores or otherwise maintains configuration information associated with the consumable. In this regard, the configuration information is utilized by the infusion device to influence operation of the infusion device to deliver fluid. For example, the configuration information may quantify or otherwise characterize an amount or rate of fluid deliverable from the consumable per a unit of actuation of a pumping mechanism configured to dispense fluid from the reservoir, with a control module of the infusion device using the configuration information to modulate actuation of the pumping mechanism to achieve a desired amount or rate of fluid delivery in accordance with the configuration information. Thus, an infusion device may be capable of supporting consumables having pumping mechanisms of different sizes or dimensions. For example, one version of a consumable component may be configured to deliver 0.25 units of insulin for a given amount of actuation of its associated pumping mechanism (e.g., per stroke of a piston in a piston pump), while a second version of the consumable component is configured to deliver one unit of insulin for the same amount of actuation of its associated pumping mechanism. Similarly, dimensions of the tubing or fluid conduits associated with a peristaltic pump may be similarly varied but accounted for via associated calibration data, thereby enabling an infusion device to support different tube diameters of different consumables that may be utilized with the infusion device.

In exemplary embodiments, the fluid infusion device includes an interface that is configured to read, scan, engage, or otherwise access the readable element of the consumable, and thereby, allow the control module of the fluid infusion device to obtain the consumable configuration information from the readable element via the interface. Thus, when the consumable engaged with the infusion device is changed, the control module may update the consumable configuration information being utilized onboard the infusion device by retrieving configuration information associated with the current consumable and thereafter utilize the updated consumable configuration information to adjust actuation of the pumping mechanism and achieve a desired amount or rate of fluid delivery from the new consumable. In this regard, updating the configuration information accounts for variations from one consumable to the next and allows the infusion device to modify actuation to maintain consistent control and delivery of fluid independent of the consumable variations.

Figure 4:
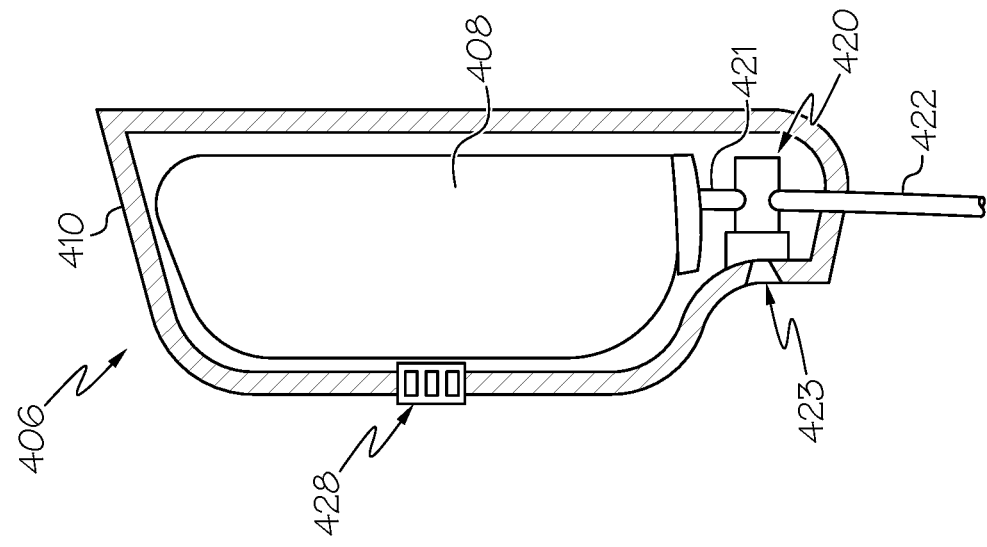
FIG. 4 depicts a plan view of a fluid infusion device and consumable suitable for use in the infusion system of FIG. 1 in conjunction with the control process of FIG. 2 and the calibration process of FIG. 3 in accordance with one or more embodiments.
Figure 4:
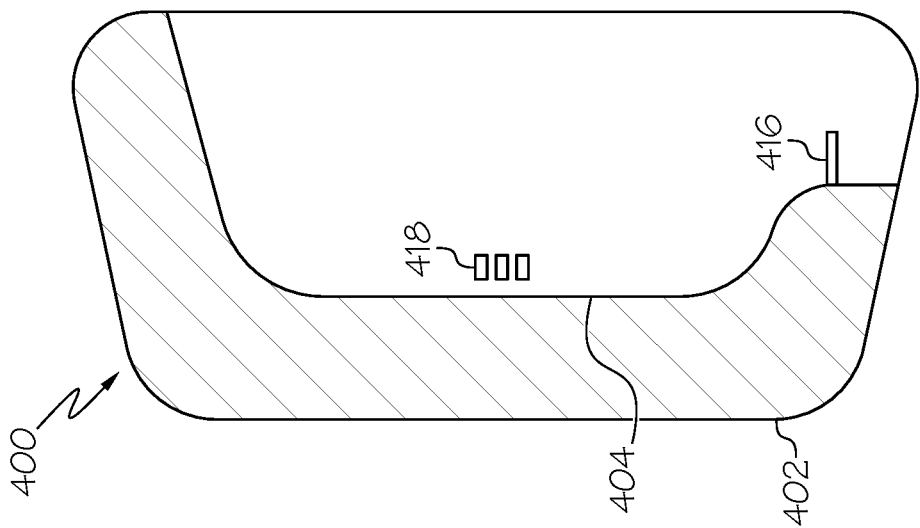
Figure 5:
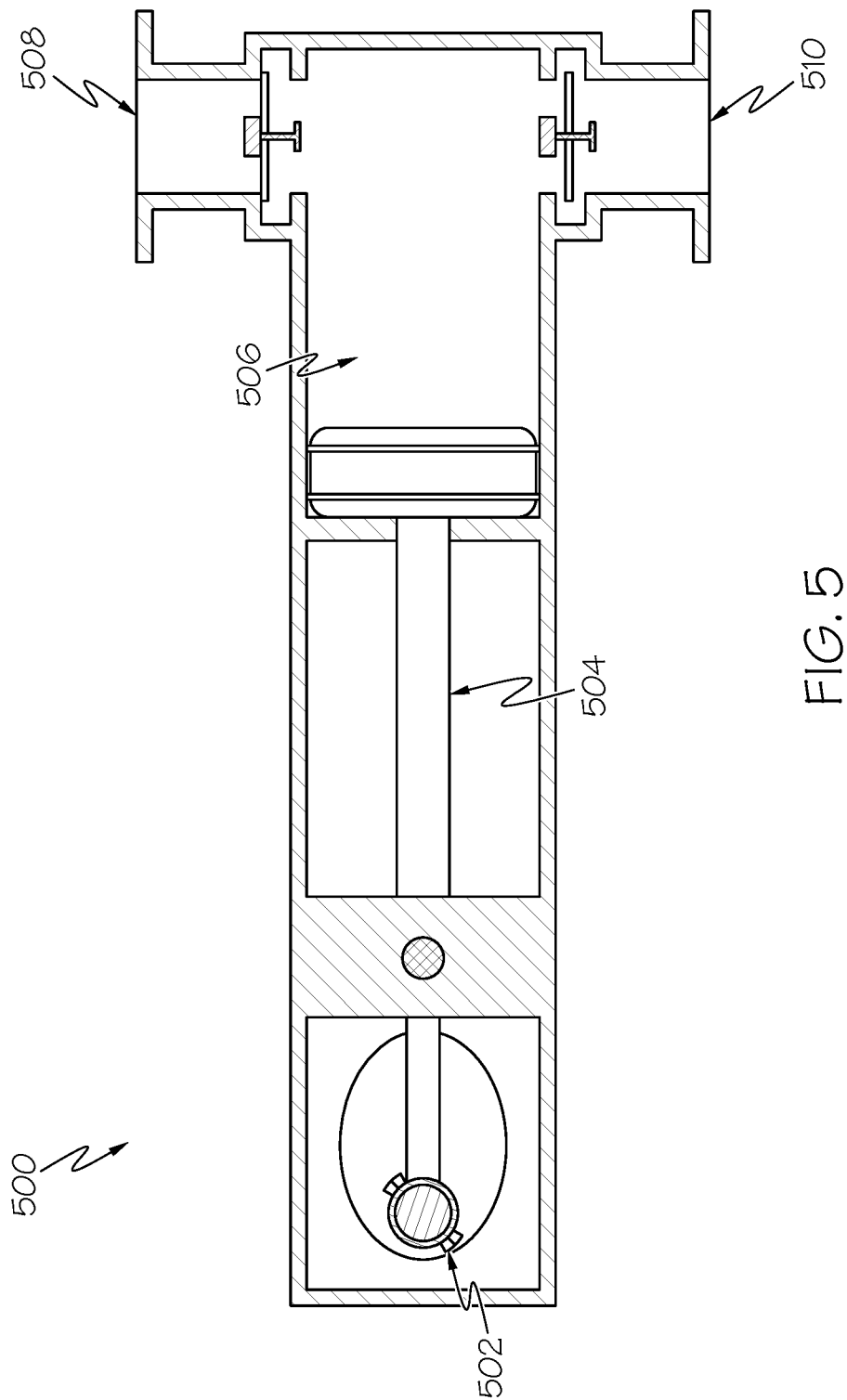
FIG. 5 depicts a plan view of a piston pumping mechanism suitable for implementation in the consumable of FIG. 4 in accordance with one or more embodiments.

For example, as described in the context of FIGS. 4-5, in one embodiment, the pumping mechanism is realized as a piston pump integrated with the reservoir as part of the consumable, where the configuration information associated with the consumable indicates the volume of fluid delivered per stroke (or stroke increment) of the piston. In this regard, different instances of the piston pump may deliver different amounts of fluid based on variations in the dimensions of the chamber, ports or valves, the piston, and other components of the piston pump. Accordingly, each consumable is pre-calibrated to identify the volume of fluid delivered per stroke (or stroke increment) of its associated piston. The infusion device reads the stroke calibration information and for a given amount of fluid to be delivered, calculates the appropriate number of strokes (or stroke increments) to achieve a desired amount of fluid using the current consumable. Accordingly, the manufacturing tolerances and other requirements for the piston and other components of the pumping mechanism may be relaxed and compensated for by the calibration information, thereby reducing costs and complexity of the consumable without compromising control of fluid delivery.

In another example embodiment, as described in the context of FIGS. 6-9, in other embodiments, the pumping mechanism is realized as a peristaltic pump includes a fluid tube from the reservoir of the consumable. In such embodiments, the configuration information associated with the consumable indicates the volume of fluid delivered per rotation (or increment thereof) of the rotor of the peristaltic pumping mechanism. In this regard, the dimensions (e.g., the diameter) of the fluid tube may vary across instances of consumables, so that different rates or amounts of fluid may be delivered as the rotor rotates. Thus, each consumable is pre-calibrated to identify the volume of fluid delivered per rotation (or rotational increment). Depending on the embodiment, the rotor of the peristaltic pumping mechanism may be integrated with the infusion device or the consumable. In embodiments where the rotor of the peristaltic pump is integrated with the consumable, it should be appreciated that the calibration information accounts not only for variations in the fluid tube dimensions across consumables, but also variations associated with the peristaltic pump rotor across consumables. Accordingly, the manufacturing tolerances and other requirements for the tubing, the peristaltic pump rotor (when part of the consumable), and other components of the consumable may be relaxed and compensated for by the calibration information, which, again, may reduce cost and complexity without compromising fluid delivery.

FIG. 1 depicts an exemplary embodiment of an infusion system 100 that includes, without limitation, a fluid infusion device 102, a sensing arrangement 104, and a consumable component 106. The fluid infusion device 102 and the consumable component 106 cooperate to deliver fluid from a reservoir 108 of the consumable 106 to the body 110 of a user (or patient). The components of an infusion system 100 may be realized using different platforms, designs, and configurations, and the embodiments depicted herein are not exhaustive or limiting. In practice, the infusion device 102 and the sensing arrangement 104 may be secured at desired locations on the body 110 of the user. In this regard, the infusion device 102 is designed as a portable medical device suitable for infusing a fluid, a liquid, a gel, or other agent into the body of a user. In exemplary embodiments described herein, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

In exemplary embodiments, the infusion device 102 is capable of controlling or otherwise regulating a physiological condition in the body 110 of a user to a desired (or target) value or otherwise maintain the condition within a range of acceptable values in an automated or autonomous manner. In one or more exemplary embodiments, the condition being regulated is sensed, detected, measured or otherwise quantified by the sensing arrangement 104 communicatively coupled to the infusion device 102. However, it should be noted that in alternative embodiments, the condition being regulated may be correlative to the measured values obtained by the sensing arrangement 104. That said, for clarity and purposes of explanation, the subject matter may be described herein in the context of the sensing arrangement 104 being realized as a glucose sensing arrangement that senses, detects, measures or otherwise quantifies the user's glucose level, which is being regulated in the body 110 of the user by the infusion device 102.

In exemplary embodiments, the sensing arrangement 104 includes one or more interstitial glucose sensing elements that generate or otherwise output electrical signals having a signal characteristic that is correlative to, influenced by, or otherwise indicative of the relative interstitial fluid glucose level in the body 110 of the user. The output electrical signals are filtered or otherwise processed to obtain a measurement value indicative of the user's interstitial fluid glucose level. In exemplary embodiments, a blood glucose meter 130, such as a finger stick device, is utilized to directly sense, detect, measure or otherwise quantify the blood glucose in the body 110 of the user. In this regard, the blood glucose meter 130 outputs or otherwise provides a measured blood glucose value that may be utilized as a reference measurement for calibrating the sensing arrangement 104 and converting a measurement value indicative of the user's interstitial fluid glucose level into a corresponding calibrated blood glucose value. For purposes of explanation, a blood glucose value calculated based on the electrical signals output by the sensing element(s) of the sensing arrangement 104 may alternatively be referred to herein as the sensor glucose value, the sensed glucose value, or variants thereof.

In the illustrated embodiment, the control module 112 generally represents the electronics and other components of the infusion device 102 that control operation of the fluid infusion device 102 according to a desired infusion delivery program in a manner that is influenced by the sensed glucose value indicative of a current glucose level in the body 110 of the user. For example, to support a closed-loop operating mode, the control module 112 maintains, receives, or otherwise obtains a target or commanded glucose value, and automatically generates or otherwise determines dosage commands for operating an actuation arrangement 116 to actuate or otherwise operate a pumping mechanism 120 and deliver insulin from the reservoir 108 to the body 110 of the user based on the difference between a sensed glucose value and the target glucose value. In other operating modes, the control module 112 may generate or otherwise determine dosage commands configured to maintain the sensed glucose value below an upper glucose limit, above a lower glucose limit, or otherwise within a desired range of glucose values. In practice, the infusion device 102 may store or otherwise maintain the target value, upper and/or lower glucose limit(s), and/or other glucose threshold value(s) in a data storage element accessible to the control module 112.

The target glucose value and other threshold glucose values may be received from an external component or be input by a user via a user interface element 140 associated with the infusion device 102. In practice, the one or more user interface element(s) 140 associated with the infusion device 102 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 140 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 1 depicts the user interface element(s) 140 as being separate from the infusion device 102, in practice, one or more of the user interface element(s) 140 may be integrated with the infusion device 102. Furthermore, in some embodiments, one or more user interface element(s) 140 are integrated with the sensing arrangement 104 in addition to and/or in alternative to the user interface element(s) 140 integrated with the infusion device 102. The user interface element(s) 140 may be manipulated by the user to operate the infusion device 102 to deliver correction boluses, adjust target and/or threshold values, modify the delivery control scheme or operating mode, and the like, as desired.

Depending on the embodiment, the control module 112 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the control module 112 includes or otherwise accesses a data storage element 114 or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the control module 112. The computer-executable programming instructions, when read and executed by the control module 112, cause the control module 112 to perform or otherwise support the tasks, operations, functions, and processes described herein. The memory 114 may also store or otherwise maintain target glucose values, glucose thresholds, consumable configuration data, and any other data or information described herein in context of the control module 112 and related processes described herein.

In exemplary embodiments, the actuation arrangement 116 includes a motor 117 that is operable to displace, actuate or otherwise operate a pumping mechanism 120 and provide a desired amount of fluid from the reservoir 108 to the body 110 of the user. In the illustrated embodiment, the motor 117 engages the pumping mechanism 120 via one or more drive element(s) 119, however, in some embodiments, the motor 117 may engage the pumping mechanism 120 directly. The drive element(s) 119 may include linkages, gears, or other components configured to translate rotational motion of a rotor of the motor 117 into a translational displacement or other movement that provides actuation of the pumping mechanism 120. Additionally, although FIG. 1 depicts the pumping mechanism 120 as being separate from the infusion device 102 and integrated with the consumable 106, in alternative embodiments, one or more aspects of the pumping mechanism 120 may be integrated with the infusion device 102 and/or the actuation arrangement 116. That said, the subject matter may be described herein primarily in the context of the pumping mechanism 120 being integrated with the consumable 106 and/or the reservoir 108.

The illustrated pumping mechanism 120 interfaces or engages a conduit 121 for fluid exiting the reservoir 108, and the pumping mechanism 120 is configured so that actuation of the pumping mechanism 120 dispenses fluid from the reservoir 108 via the conduit 121 and results in the delivery of the fluid to the body 110 of the user via a fluid delivery path provided by an infusion arrangement 122. In this regard, the infusion arrangement 122 may include one or more tubes, needles, cannulas, infusion sets, or the like that provides a path for fluid communication from the exit conduit 121 of the reservoir 108 to the body 110 of the user. The control module 112 commands, signals, or otherwise operates the motor 117 (or a driver associated therewith) to cause the rotor of the motor to rotate by an amount that produces a corresponding amount of actuation of the pumping mechanism 120 (via a drive element(s) 119) that results in the delivery of a commanded dosage of fluid from the reservoir 108. For example, the control module 112 may determine an amount of actuation of the pumping mechanism 120 that achieves a commanded dosage based on pumping mechanism calibration data as described below, and then determine a corresponding amount of rotation of the rotor required to produce that amount of actuation of the pumping mechanism 120.

In exemplary embodiments, the control module 112 receives or otherwise obtains configuration data or information pertaining to the current consumable 106 and utilizes the configuration data to calculate the amount of actuation of the pumping mechanism 120 required to deliver a commanded dosage of fluid, and then determines a corresponding amount of actuation of the actuation arrangement 116 and/or motor 117 to achieve that commanded delivery of fluid. In this regard, the configuration data may include calibration data that characterizes or quantifies the relationship between an amount of actuation of the pumping mechanism 120 and a corresponding amount of fluid delivered from the reservoir 108 for a given consumable 106. Additionally, the configuration data may include physical measurement data associated with one or more elements or components of the pumping mechanism 120, such as, for example, the linear dimension of a piston pump chamber, the inner diameter or circumference of piston pump chamber, the inner diameter or circumference of a fluid conduit or tubing associated with the pumping mechanism 120, and the like. In this regard, some embodiments may utilize the measurements of physical dimensions associated with the pumping mechanism 120 in concert with calibration data associated with the pumping mechanism 120 to improve the precision or accuracy of fluid delivery associated with operation of the pumping mechanism 120. In exemplary embodiments, the infusion device 102 includes an interface 118 coupled to the control module 112 that is configured to read or otherwise obtain the configuration data associated with the consumable 106 from a readable element 124 integrated or incorporated with the consumable 106. That said, in some embodiments, the configuration data associated with the consumable 106 may be input or provided via a user interface element 140.

It should be appreciated that any number of potential combinations of readable elements 124 and corresponding interfaces 118 may be utilized in a practical embodiment of the infusion system 100. For example, in one embodiment, the readable element 124 is realized as a radio frequency identification (RFID) tag integrated with the consumable 106, where the interface 118 is realized as an RFID reader. In another embodiment, the readable element 124 is realized as a barcode provided on or otherwise integrated with a surface of the consumable 106, where the interface 118 is realized as a barcode scanner. In another embodiment, the readable element 124 may be realized as a data storage element (e.g., an EEPROM or other readable memory) that is coupled to an electrical bus, one or more electrical terminals, or another communications interface that engages with a corresponding communications interface 118 of the infusion device 102 when the consumable 106 is engaged with or coupled to the infusion device 102. For example, in one embodiment, the interface 118 supports wireless communications with a corresponding communications interface of the consumable 106, and the control module 112 is configured to automatically establish wireless communications with the consumable 106 when the consumable is within communications range and engaged with the infusion device 102 to wirelessly retrieve or receive the calibration data from the readable element 124. That said, it should be appreciated that the subject matter described herein is not intended to be limited to any particular type of readable, detectable, or otherwise identifiable element and corresponding interface. In one or more exemplary embodiments, the calibration data is maintained by the readable element 124 in an encrypted form that is capable of being decrypted by the control module 112 of the infusion device 102 using one or more keys stored or otherwise maintained in memory 114.

It should be appreciated that FIG. 1 is a simplified representation of the infusion device 102 for purposes of explanation and is not intended to limit the subject matter described herein in any way. In this regard, depending on the embodiment, some features and/or functionality of the sensing arrangement 104 may implemented by or otherwise integrated into the control module 112, or vice versa. Furthermore, some of the features and/or functionality of the control module 112 may be implemented by a remote computing device that is physically distinct and/or separate from the infusion device 102, such as, for example, a computing device, a mobile device, a server, or the like.

Figure 2:
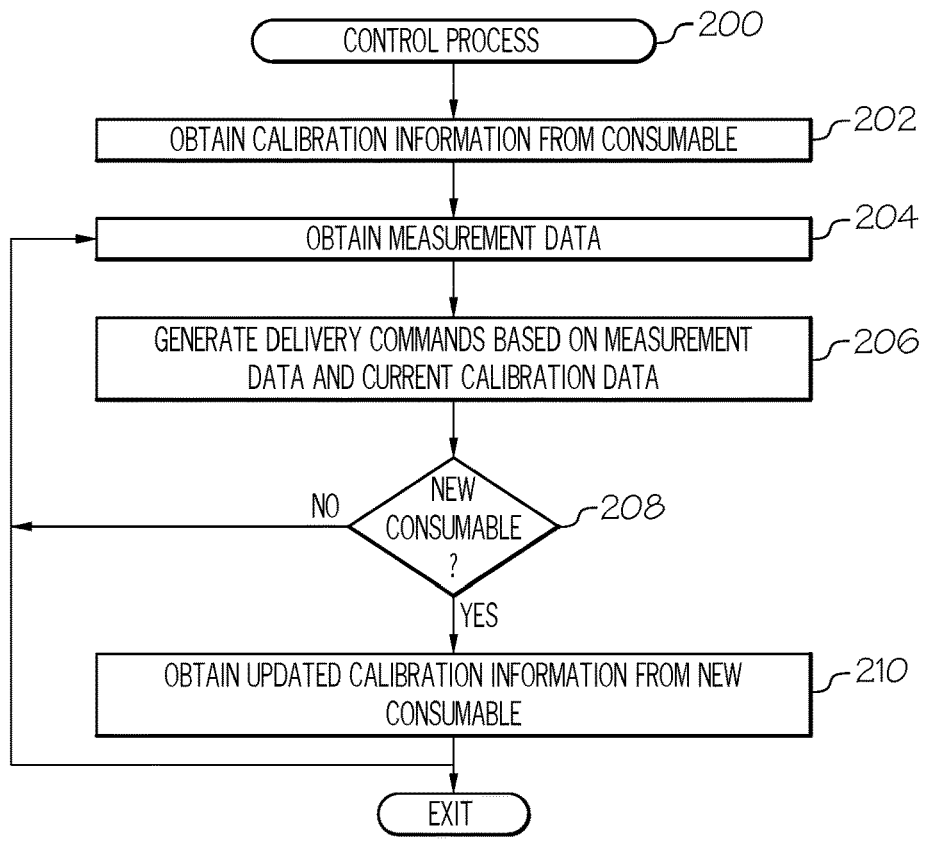
FIG. 2 is a flow diagram of an exemplary control process suitable for use with the infusion system of FIG. 1 in one or more exemplary embodiments.

FIG. 2 depicts an exemplary control process 200 suitable for implementation by a control system associated with an electronic device, such as a control module 112 in an infusion device 102, to adaptively control operation of the device based on calibration information associated with a current consumable. The various tasks performed in connection with the control process 200 may be performed by hardware, firmware, software executed by processing circuitry, or any combination thereof. For illustrative purposes, the following description refers to elements mentioned above in connection with FIG. 1. In practice, portions of the control process 200 may be performed by different elements of an infusion system 100, however, for purposes of explanation, the control process 200 may be described herein primarily in the context of the infusion device 102 and the control module 112. It should be appreciated that the control process 200 may include any number of additional or alternative tasks, the tasks need not be performed in the illustrated order and/or the tasks may be performed concurrently, and/or the control process 200 may be incorporated into a more comprehensive procedure or process having additional functionality not described in detail herein. Moreover, one or more of the tasks shown and described in the context of FIG. 2 could be omitted from a practical embodiment of the control process 200 as long as the intended overall functionality remains intact.

The illustrated control process 200 receives or otherwise obtains the calibration information associated with the consumable currently engaged with the infusion device, receives or otherwise obtains measurement data associated with the physiological condition being controlled or regulated by the infusion device, and determines or otherwise generates commands for operating the infusion device to deliver fluid based at least in part on the currently-applicable calibration information and the measurement data (tasks 202, 204, 206). In this regard, in one or more embodiments, the control module 112 operates the interface 118 to access or otherwise read the readable element 124 to obtain the calibration data associated with the current consumable 106 each time the control scheme or operating mode implemented by the control module 112 is updated to generate a delivery command. For example, in response to receiving an updated measurement from the sensing arrangement 104, the control module 112 may automatically operate the interface 118 to read, scan, or otherwise access the calibration data maintained by the readable element 124. That said, in other embodiments, the control module 112 automatically operates the interface 118 to access, scan, or otherwise read the readable element 124 of the consumable 106 in response to an instance of the consumable 106 being inserted into, engaged with, or otherwise coupled to the housing of the infusion device 102. For example, some embodiments of the infusion device 102 may include one or more sensors or other elements that are coupled to the control module 112 and configured to detect the presence or engagement of the consumable 106 with the infusion device 102 and provide a corresponding indication to the control module 112. In response to receiving a signal or indication of a consumable 106 being engaged with the infusion device 102, the control module 112 automatically operates the interface 118 to read, scan, or otherwise access the calibration data maintained by the readable element 124.

In one or more exemplary embodiments, the control module 112 calculates or otherwise determines an amount or rate of fluid to be delivered from the reservoir 108 based on a relationship between the measurement value(s) received from the sensing arrangement 104 and one or more target or reference values for the physiological condition of the user. For example, for closed-loop glucose control, the control module 112 determines an amount of insulin to be delivered based on the difference between a current sensed glucose measurement value received from the sensing arrangement 104 and a target glucose measurement value for the user. After the desired (or commanded) dosage of insulin is determined, the control module 112 calculates or otherwise determines a corresponding amount of actuation of the pumping mechanism 120 that provides that desired dosage based on the calibration data associated with the consumable 106. In this regard, the calibration data may include a conversion factor for converting a dosage value from units of insulin to a corresponding amount of actuation (or number of actuation increments) of the pumping mechanism 120 and/or the actuation arrangement 116. In some embodiments, the control module 112 may utilize additional calibration information associated with the actuation arrangement 116 and/or the motor 117 to convert an amount of actuation of the pumping mechanism 120 to a corresponding amount of actuation (or number of actuation increments) of the actuation arrangement 116 and/or the motor 117. The resulting delivery command determined by the control module 112 using the consumable calibration data represents a commanded amount of actuation of the actuation arrangement 116 and/or the motor 117, which produces a corresponding amount of actuation of the pumping mechanism 120 engaged with the exit conduit 121 of the reservoir 108 to dispense the commanded dosage amount of insulin from the reservoir 108 to the infusion arrangement 122.

In exemplary embodiments, the loop defined by tasks 204, 206, and 208 repeats indefinitely until an instance of the consumable is removed (e.g., when the reservoir 108 becomes depleted) and replaced with a new instance of the consumable. Thereafter, in response to detecting or otherwise identifying a new instance of the consumable being utilized with the infusion device, the control process 200 continues by receiving or otherwise obtaining updated calibration information associated with the new consumable currently engaged with the infusion device and determines or otherwise generates commands for operating the infusion device to deliver fluid based at least in part on the updated calibration information and the subsequently-received measurement data (tasks 204, 206, 208, 210). For example, in embodiments where the infusion device 102 includes a sensor that detects or otherwise identifies presence of a consumable 106, the control module 112 may automatically detect the removal of a first consumable 106 and insertion of a second consumable 106 based on the output of the sensor, and in response, operate the interface 118 to retrieve updated calibration data associated with the new instance of the consumable 106 in a similar manner as described above. That said, other embodiments may access, scan, or otherwise read the readable element 124 to obtain updated calibration data associated with the new consumable 106 on the next iteration of the control scheme or operating mode implemented by the control module 112 updating the delivery commands (e.g., in response to receiving an updated measurement from the sensing arrangement 104).

The loop defined by tasks 204, 206, and 208 may again repeat until the current instance of the consumable is removed and replaced with a new instance of the consumable. In this regard, each time the consumable is changed, the calibration data and/or conversion factor(s) utilized by the control module 112 to convert a commanded dosage of insulin into a corresponding commanded actuation of the actuation arrangement 116 and/or motor 117 is updated to reflect the current instance of the consumable 106. In this manner, the control process 200 is adaptive and accounts for variations in the physical characteristics of the current instance of the consumable 106 relative to preceding instances of the consumable 106. For example, the dimensions of the conduit 121 for fluid exiting the reservoir 108 which is engaged with the pumping mechanism 120 and/or the infusion arrangement 122 may vary from one instance of the consumable 106 to the next, which, in turn, results in variations in the amount or rate of insulin delivered per unit of actuation of the pumping mechanism 120 that engages with the exit conduit 121. Thus, adaptively updating the calibration data facilitates maintaining precise or accurate delivery of insulin from different instances of the consumable 106 regardless of the fluid conduit 121 dimensions.

Figure 3:
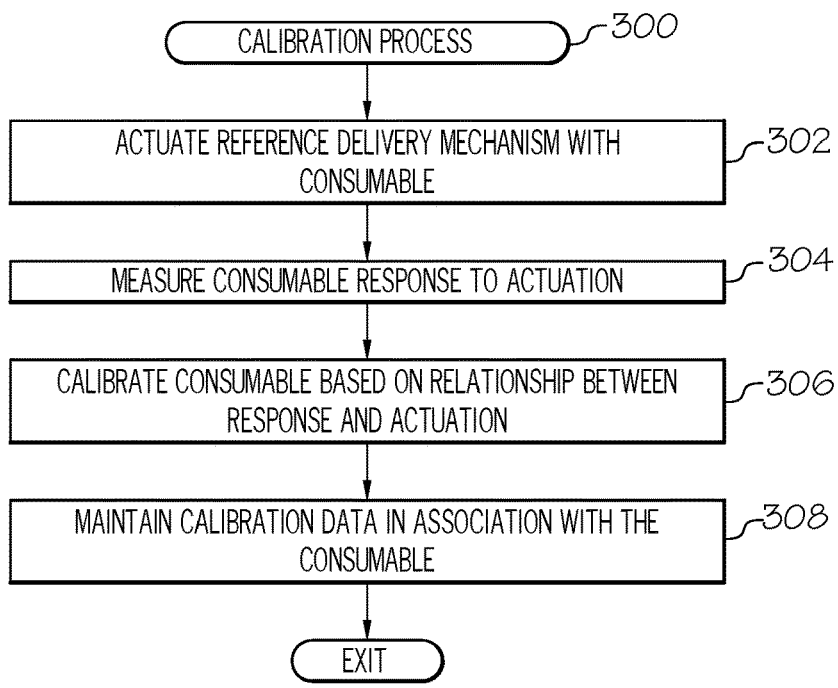
FIG. 3 is a flow diagram of an exemplary calibration process suitable for use with the control process of FIG. 2 in one or more exemplary embodiments.

FIG. 3 depicts an exemplary calibration process 300 for determining calibration information associated with a consumable and maintaining the association of the calibration information with the consumable. The various tasks performed in connection with the calibration process 300 may be performed by hardware, firmware, software executed by processing circuitry, or any combination thereof. For illustrative purposes, the following description refers to elements mentioned above in connection with FIG. 1. In practice, portions of the calibration process 300 may be performed by different elements of an infusion system 100, however, for purposes of explanation, the calibration process 300 may be described herein primarily in the context of the infusion device 102 and the control module 112. It should be appreciated that the calibration process 300 may include any number of additional or alternative tasks, the tasks need not be performed in the illustrated order and/or the tasks may be performed concurrently, and/or the calibration process 300 may be incorporated into a more comprehensive procedure or process having additional functionality not described in detail herein. Moreover, one or more of the tasks shown and described in the context of FIG. 3 could be omitted from a practical embodiment of the calibration process 300 as long as the intended overall functionality remains intact.

In exemplary embodiments, the calibration process 300 actuates or otherwise operates a reference drive system engaged with the pumping mechanism consumable being calibrated to achieve some reference amount of actuation of the pumping mechanism and monitors or otherwise measures the response of the consumable to the reference actuation of the pumping mechanism (tasks 302, 304). In this regard, the consumable 106 being calibrated may be configured or otherwise arranged so that its pumping mechanism 120 engages or otherwise interfaces with a reference instance of the actuation arrangement 116, which is then actuated by some reference amount to impart a corresponding force or action on the pumping mechanism 120 and/or the fluid conduit 121 exiting the reservoir 108. For example, depending on the embodiment, the reference amount of actuation could correspond to a single revolution of a rotor of the motor 117 or the pumping mechanism 120, a single stroke or instance of linear motion of the drive element(s) 119 or the pumping mechanism 120, or some other increment of actuation. In this regard, some embodiments of the pumping mechanism 120 may be calibrated for fractional revolutions or rotations, partial strokes, or the like.

A sensing element may be provided downstream of the pumping mechanism 120 to quantify, sense, or otherwise measure the fluid response to the reference amount of actuation. For example, the exit conduit 121, pumping mechanism 120, and/or a reference infusion arrangement 122 may receive or otherwise be equipped with a flow meter that measures a rate or amount of fluid dispensed via the exit conduit 121 in response to the reference actuation of the pumping mechanism 120. In this regard, depending on the embodiment, the fluid may be the fluid to be dispensed from the reservoir (e.g., insulin) or some other reference fluid (e.g., ambient air from an empty reservoir). For example, the reservoir 108 may be filled with the fluid to be dispensed after calibration of the consumable 106. It should be appreciated that for embodiments where the dispensed fluid during calibration (e.g., air) is different from the fluid to be delivered during subsequent operation (e.g., insulin), one or more conversion factors may be applied to the measured fluid flow to more accurately characterize the likely response of the operative fluid to the reference amount of actuation. As another example, a pressure sensor may be provided downstream of the pumping mechanism 120 to measure an increase in pressure in response to the reference actuation of the pumping mechanism 120, which, in turn, may be converted from a pressure measurement to a corresponding amount of fluid delivery. It should be appreciated that numerous different techniques for measuring the fluid response to the reference actuation of the pumping mechanism, and the subject matter described herein is not intended to be limited to any particular manner of calibrating the consumable 106.

The calibration process 300 continues by calibrating the consumable based on the relationship between the measured response and the reference actuation and storing or otherwise maintaining the calibration data in association with the consumable (tasks 306, 308). For example, the control module 112 associated with the reference instance of the pumping mechanism 120 may receive or otherwise obtain the measured response to the reference actuation of the pumping mechanism 120 and then calculate or otherwise determine one or more calibration conversion factors for converting an amount of actuation of the pumping mechanism 120 to a corresponding amount of fluid dispensed from the consumable 106. In this regard, it should be noted that in practice, any number of instances of reference actuations and measured responses may be utilized in determining the calibration data associated with a particular consumable 106, for example, by averaging the measured responses or performing other statistical processes to improve the accuracy or reliability of the resulting calibration data.

Once the calibration data associated with the consumable 106 is determined, the calibration data is stored or otherwise maintained by the readable element 124 associated with the consumable 106. For example, a control module 112 associated with the reference instance of the pumping mechanism 120 may operate an associated interface 118 to write or otherwise store the calibration data to the readable element 124 of the consumable 106. That said, in other embodiments, the readable element 124 may be configured to store or maintain the calibration data before being coupled to or otherwise engaged with the consumable 106. In yet other embodiments, the calibration data may be printed, impressed, embossed, or otherwise transferred to the housing of the consumable 106 to achieve the readable element 124. In one or more embodiments, the calibration data is maintained by the readable element 124 in an encrypted form that may be decrypted by a control module 112 of an infusion device 102 using one or more cryptographic keys, which may be stored locally onboard the infusion device 102 (e.g., in memory 114) or remotely and retrieved via a network in accordance with a key exchange procedure.

In one or more embodiments, physical measurements of one or more elements or components of the pumping mechanism 120 may also be obtained during the calibration process 300 and stored or otherwise be maintained by the readable element 124 in addition to the calibration data. For example, a diameter or other dimension of a fluid path or chamber associated with the pumping mechanism 120 (e.g., the length or linear dimension of a piston pump chamber, the inner diameter or circumference of piston pump chamber, the inner diameter or circumference of a fluid conduit or tubing of a peristaltic pump, or the like) may be measured and then stored or maintained by the readable element 124. Providing measurement data on the readable element 124 supports embodiments where the control module 112 utilizes measurements of physical dimensions associated with the pumping mechanism 120 in concert with calibration data associated with the pumping mechanism 120 to improve the precision or accuracy of fluid delivery associated with operation of the pumping mechanism 120.

After the consumable 106 is configured with a readable element 124 maintaining the determined calibration data and a reservoir 108 containing the operative fluid to be dispensed, the consumable 106 may be deployed and utilized with an instance of the infusion device 102. That is to say, the control process 200 of FIG. 2 may be employed by an infusion device 102 that is coupled to or otherwise engaged with a consumable 106 calibrated in accordance with the calibration process 300 of FIG. 3 using a reference instance of the infusion device 102.

FIG. 4 depicts an exemplary embodiment of an infusion device 400 and consumable 406 suitable for use in the infusion system 100 of FIG. 1 in conjunction with the control process 200 of FIG. 2, where the pumping mechanism 420 (e.g., pumping mechanism 120) is integrated or incorporated with the consumable 406.

The infusion device 400 includes a housing 402 having a cutout or voided portion 404 that is contoured to conform to the housing 410 of the consumable 406. In this regard, the consumable 406 may be inserted into the cutout portion 404 of the infusion device housing 402 to engage or otherwise couple the consumable 406 to the infusion device 400. In practice, the housing 402 may include one or more features configured to secure or otherwise fix the consumable 406 in an engaged position during operation of the infusion device 400.

The infusion device 400 includes an exposed drive element 416 that is configured to engage with the pumping mechanism 420 of the consumable 406. In this regard, the drive element 416 may be a component of a drive element(s) 119 that engages with the pumping mechanism 420 to actuate the pumping mechanism 420 in response to actuation of a motor 117 housed or otherwise contained within the infusion device housing 402. For example, the drive element 416 may be realized as a shaft or linkage that protrudes from the infusion device housing 402 into a voided area defined by the cutout portion 404 at a location corresponding to the drive mechanism 420 when a consumable 406 is inserted in the housing 402. In this regard, the consumable housing 410 and/or the drive mechanism 420 may include a port or receptacle 423 configured to receive the drive element 416 that is aligned with the drive element 416 when the consumable 406 is engaged with the infusion device 400.

The infusion device 400 also includes an exposed interface 418 (e.g., interface 418) that is adjacent or otherwise proximate to the cutout portion 404 at a location aligned with a readable element (or a corresponding interface 428 thereto) associated with the consumable 406. For example, the interface 418 may be realized as one or more pins, pads, ports, wires, or other electrical interconnects that are integrated with the surface of the cutout portion 404 of the infusion device housing 402 and configured to mate, engage, or otherwise interface with a corresponding interface 428 provided on or otherwise integrated with an opposing surface of the consumable housing 410. In such embodiments, the readable element 124 may be realized as a data storage element or memory (e.g., an EPROM) that is housed or otherwise contained within the consumable housing 410 and capable of being read by a control module 112 housed or contained within the infusion device housing 402 via the interfaces 418, 428. That said, in other embodiments, the interface 418 may be realized as an RFID reader, a barcode scanner, or some other interface capable of reading or retrieving configuration data maintained on or in the consumable housing 410 without utilizing the interface 428. For example, an RFID tag may be integrated within or affixed to the consumable housing 410 at a corresponding location so that the configuration data may be read from the RFID tag by an RFID reader interface 418 when the consumable 406 is inserted into the infusion device housing 402.

Still referring to FIG. 4, the consumable housing 410 is configured to house, support, or otherwise retain a fluid reservoir 408 that is in fluid communication with an infusion arrangement 422 via an exit conduit 421 and the pumping mechanism 420. For example, in one embodiment, the pumping mechanism 420 is realized as a piston pump that includes a suction port (or inlet) that mates or engages with the exit conduit 421 to receive fluid from the reservoir 408 and a discharge port (or outlet) that mates or engages with the infusion arrangement 422 to dispense or otherwise deliver fluid in response to actuation of the piston. In this regard, the calibration data associated with the consumable 406 may account for variations in the dimensions of the exit conduit 421, the suction and/or discharge ports of the piston, and/or the chamber of the piston pump. Thus, while different amounts of fluid may be dispensed by the pumping mechanism 420 in response to a single stroke (or incremental stroke) of the piston across various instances of the consumable 406, the calibration data associated with the current consumable 406 may be utilized by the control module 112 of the infusion device 102, 400 to adjust actuation or operation of the actuation components 116, 117, 119, 416 to achieve a desired dosage of fluid delivery as described above.

For example, using the respective calibration data associated with different instances of the consumable 406, the control module 112 may generate commands for actuating one instance of the pumping mechanism 420 that delivers 0.5 units of insulin in a full stroke by 10% of a stroke to achieve a desired insulin delivery of 0.05 units, while for another instance of the pumping mechanism 420 that delivers 0.55 units of insulin in a full stroke, the control module 112 generates commands for actuating that instance of the pumping mechanism 420 by 9% of a stroke to achieve a desired insulin delivery of 0.05 units. Thus, variations associated with the pumping mechanism 420 of the consumables 406 (e.g., when an instance of the pumping mechanism 420 designed or intended to deliver 0.5 units of insulin in a full stroke actually delivers 0.55 units of insulin per stroke after fabrication) may be compensated for using the calibration data, thereby relaxing tolerances when manufacturing the pumping mechanisms 420 and/or consumables 406.

Similarly, the control module 112 may utilize the calibration data to accommodate different consumables 406 supporting different volumes or rates of fluid delivery or otherwise having differently sized pumping mechanisms 420. For example, when the infusion device 400 receives an instance of the consumable 406 that delivers 1.0 units of insulin in a full stroke, the control module 112 may generate commands for actuating its associated pumping mechanism 420 by 5% of a stroke to achieve a desired insulin delivery of 0.05 units. Thus, increased rates or volumes of delivery may be accommodated by merely using a different consumable 406.

FIG. 5 depicts an embodiment of a piston pump pumping mechanism 500 suitable for use as a pumping mechanism 120, 420 associated with operation of an infusion device 102, 400 in conjunction with the processes 200, 300 described above in the context of FIGS. 1-4. The piston pump pumping mechanism 500 includes a crankshaft 502 that engages a drive element(s) 119, 416 configured to rotate the crankshaft 502 in response to rotation of a motor 117 and thereby actuate or displace a piston 504 coupled to the crankshaft 502 within a chamber 506. It should be noted the crankshaft 502 is merely one exemplary mechanism for translating rotation of a rotor to a linear displacement, and in practice, alternative mechanisms may be utilized, such as, for example, a rack and pinion mechanism, a solenoid mechanism, or the like.

A valved inlet port 508 to the chamber 506 receives or otherwise engages a conduit 421 associated with a reservoir 108, 408 to provide fluid communication between the chamber 406 and the reservoir 108, 408. A valved outlet port 510 of the chamber 506 receives or otherwise engages an infusion arrangement 122, 422 to provide a path fluid communication from the chamber 406 to the body of a user via the infusion arrangement 122, 422. Accordingly, actuation of the crankshaft 502 and the piston 504 of the piston pump pumping mechanism 500 to draw fluid from the reservoir 108, 408 into the chamber 506 and then discharge and deliver fluid from the chamber 506 to a user via the infusion arrangement 122, 422.

Referring to FIG. 5 with reference to FIGS. 1-4, in one exemplary embodiment, a consumable 106, 406 including the piston pump pumping mechanism 120, 420, 500 is calibrated for the amount of fluid dispensed and delivered from the reservoir 108, 408 per stroke of the piston 504 (or an increment thereof). For example, the consumable 106, 406 may be calibrated by actuating the crankshaft 502 to actuate the piston 504 through its full range of displacement (e.g., by achieving a full rotation of the crankshaft 502) (e.g., task 302) and then measuring the response at the outlet port 510 of the piston pump pumping mechanism 120, 420, 500 (e.g., task 304). Thereafter, a calibration conversion factor associated with that instance of the consumable 106, 406 may be determined based on the relationship of the fluid response at the outlet port 510 to the amount of actuation of the piston 504 (e.g., task 306) and stored or otherwise maintained by the readable element 124 associated with the consumable 106, 406 (e.g., task 308). Additionally, in some embodiments, measurements of one or more physical dimensions of the chamber 506 and/or one or more of the ports 508, 510 may be obtained and stored or otherwise maintained by the readable element 124 associated with the consumable 106, 406.

When the consumable 106, 406 is inserted into or engaged with the infusion device 102, 400, the control module 112 operates the interface 118, 418 to read the calibration conversion factor from the consumable 106, 406 (e.g., task 202), and then utilizes the calibration conversion factor to operate the actuation components 116, 117, 119, 416 of the infusion device 102, 400 and achieve a desired delivery of fluid to the user via the outlet port 510 and infusion arrangement 122, 422. For example, based on one or more sensor glucose measurement values received from the sensing arrangement 104, the control module 112 may determine a desired dosage of insulin to be delivered to the user. The calibration conversion factor for the current instance of the piston pump pumping mechanism 120, 420, 500 associated with the current instance of the consumable 106, 406 may be utilized to determine a commanded amount of actuation of the piston pump pumping mechanism 120, 420, 500 to achieve that desired delivery of insulin, as described above in the context of FIG. 4. Thus, the calibration conversion factor adjusts or otherwise influences the resulting amount of actuation of the piston 504 that is commanded in a manner that accounts for the physical dimensions and variations thereof associated with the current instance of the piston pump pumping mechanism 120, 420, 500, fluid conduit 421, and the like associated with the current consumable 106, 406 relative to other instances of the consumable 106, 406. Other embodiments may also utilize the physical measurement data associated with the current instance of the consumable 106, 406 to adjust or otherwise augment the amount of actuation. Thereafter, the control module 112 generates corresponding delivery commands for operating the actuation components 116, 117, 119, 416 to achieve the determined amount of actuation of the piston pump pumping mechanism 120, 420, 500 that results in the desired dosage of insulin being delivered.

Figure 6:
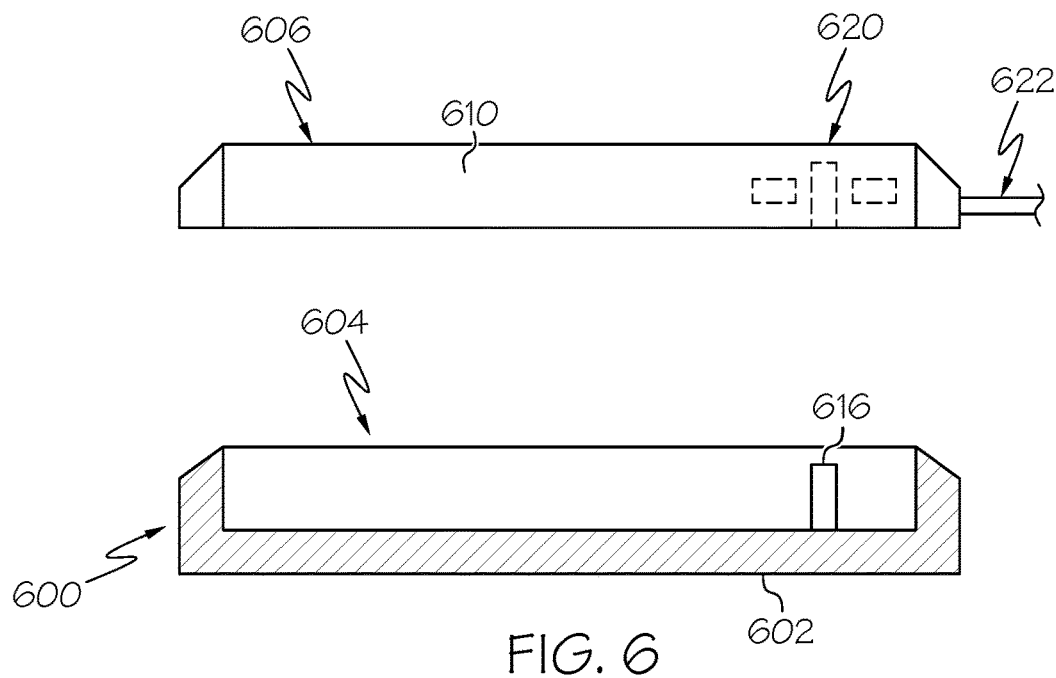
FIG. 6 depicts a plan view of another embodiment of a fluid infusion device and consumable suitable for use in the infusion system of FIG. 1 in conjunction with the control process of FIG. 2 and the calibration process of FIG. 3 in accordance with one or more embodiments where the pumping mechanism is realized as a peristaltic pumping mechanism integrated with the consumable.
Figure 7:
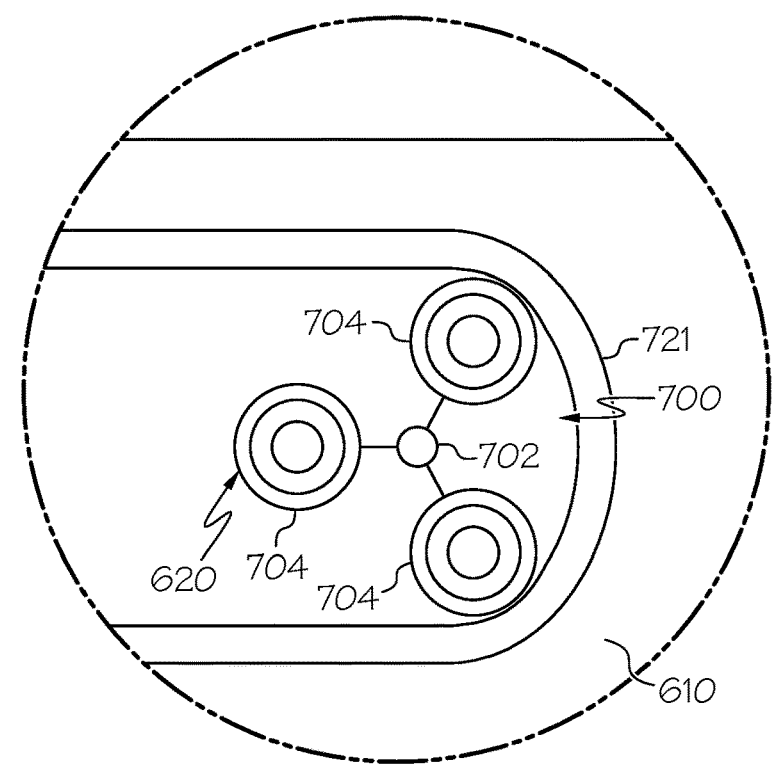
FIG. 7 depicts a detail view of the peristaltic pumping mechanism in the infusion system of FIG. 6 in accordance with one or more embodiments.

FIGS. 6-7 depict another exemplary embodiment of an infusion device 600 and consumable 606 suitable for use in the infusion system 100 of FIG. 1 in conjunction with the control process 200 of FIG. 2. In the embodiment of FIGS. 6-7, the pumping mechanism 620 (e.g., pumping mechanism 120) is realized as a peristaltic pump mechanism integrated into or incorporated with the consumable housing 610.

In a similar manner as described above in the context of FIG. 4, the infusion device housing 602 includes a cutout or voided portion 604 that is contoured to conform to the consumable housing 610, such that the consumable 606 is inserted into the cutout portion 604 of the infusion device housing 602 to engage or otherwise couple the consumable 606 to the infusion device 600. The infusion device 600 also includes an exposed drive element 616 that is configured to engage with the pumping mechanism 620 of the consumable 606. In the embodiment of FIGS. 6-7, the drive element 616 is realized as a rotary shaft that engages a rotor 700 of the peristaltic pump mechanism 620 to rotate the rotor 700 in response to actuation of an actuation arrangement 116 and/or motor 117 within the infusion device housing 602. Rollers 704 integrated with or otherwise coupled to the rotor 700 compress portions of the conduit (or tubing) 721 for fluid exiting the reservoir 108 contained within the consumable housing 610 to dispense fluid in response to rotation of the rotor 700, via rollers 704 integrated with or otherwise coupled to the rotor 700. In this regard, the tubing 721 provides a path for fluid flow from the reservoir 108 to a port or outlet of the consumable housing 610 that is configured to receive or otherwise engage an infusion arrangement 622 (e.g., infusion arrangement 122). As the rollers 704 compress and traverse the tubing 721 in response to rotation of the rotor 700, fluid is drawn into the tubing 721 from the reservoir 108 and dispensed downstream into the infusion arrangement 622. In one example embodiment, the shaft 616 is inserted into a central bore 702 of the rotor 700, and one or more of the shaft 616 and the rotor 700 includes one or more features configured to fixedly engage or couple the rotor 700 to the shaft 616.

Figure 8:
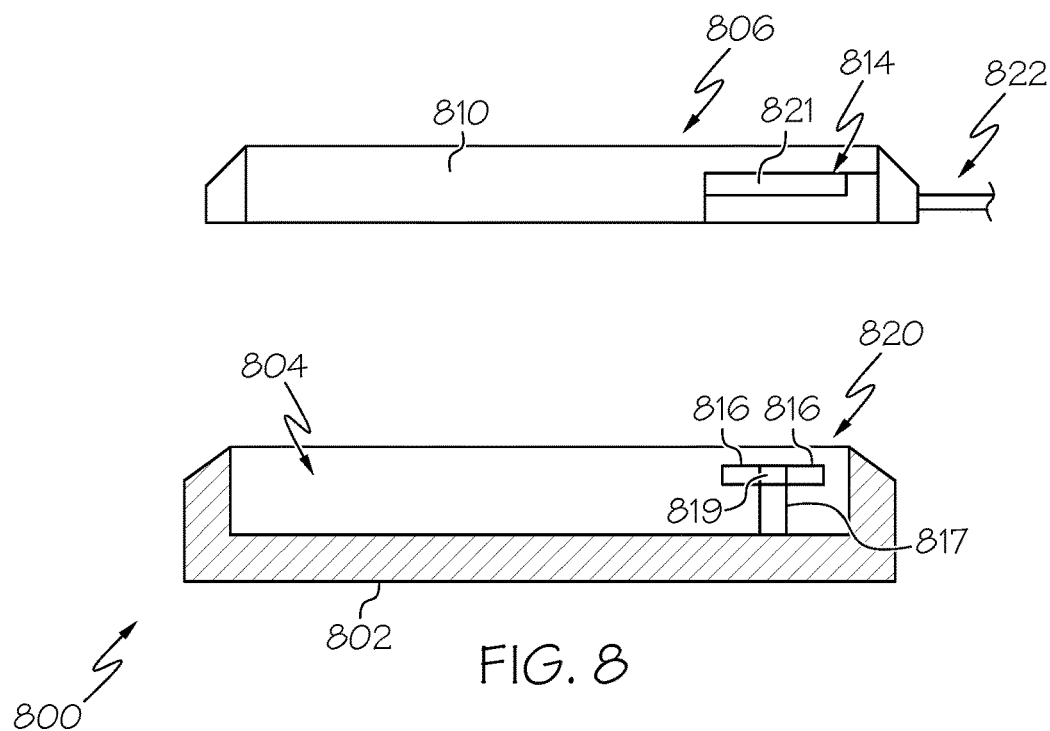
FIG. 8 depicts a plan view of another embodiment of a fluid infusion device and consumable that cooperatively support a peristaltic pumping mechanism suitable for use in conjunction with the control process of FIG. 2 and the calibration process of FIG. 3 in accordance with one or more embodiments.
Figure 9:
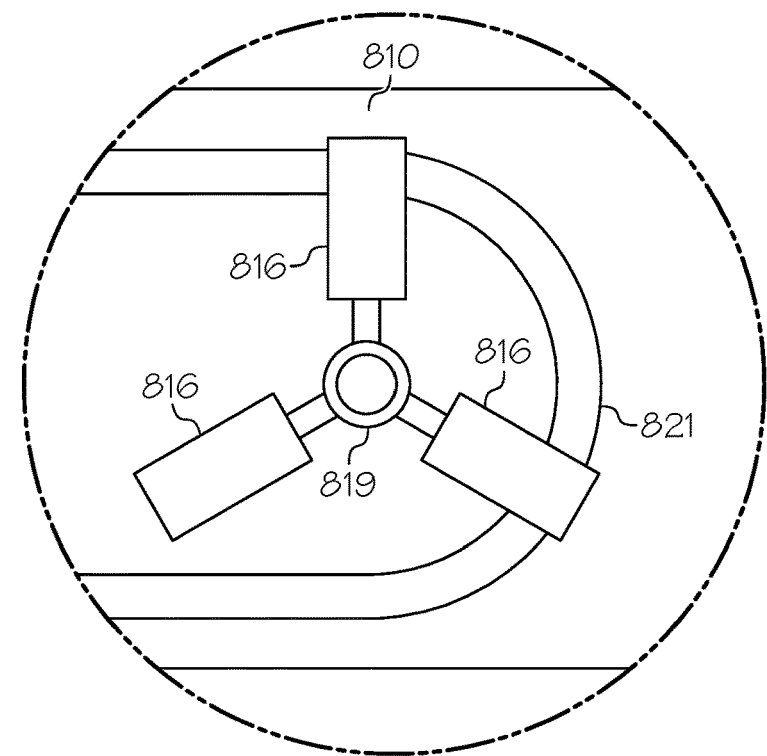
FIG. 9 depicts a detail view of the peristaltic pumping mechanism in the infusion system of FIG. 8 in accordance with one or more embodiments.

Although not illustrated in FIGS. 6-7, in a similar manner as described above, the infusion device housing 602 includes an interface 118 configured to access a readable element 124 contained within or physically associated with the consumable housing 610, to read or otherwise retrieve configuration data associated with the consumable 606, which may be calibrated in accordance with the calibration process 300 of FIG. 3. In this regard, the calibration data associated with the consumable 606 accounts for variations in the inner diameter and potentially other dimensions of the tubing 721, potential variations associated with the interface between the rollers 704 and the tubing 721, or potential variations associated with other components 700, 704 of the peristaltic pump mechanism 620. For example, the calibration data may characterize the amount of fluid delivered or dispensed from the reservoir 108 via the tubing 721 per revolution of the rotor 700. Thus, while different amounts of fluid may be dispensed by the peristaltic pump pumping mechanism 620 in response to a single rotation of the rotor 700 across various instances of the consumable 606, the calibration data associated with the current consumable 606 may be utilized by the control module 112 of the infusion device 102, 400 to adjust actuation or operation of the actuation components 116, 117, 119, 616 to achieve a desired dosage of fluid delivery as described above. In this regard, the calibration data accounts for variations associated with the inner diameter of the tubing FIGS. 8-9 depict another exemplary embodiment of an infusion device 800 and consumable 806 suitable for use in the infusion system 100 of FIG. 1 in conjunction with the control process 200 of FIG. 2. In the embodiment of FIGS. 8-9, the pumping mechanism 820 (e.g., pumping mechanism 120) is realized as a peristaltic pump mechanism that includes one or more elements or components that are integrated into or incorporated with the infusion device housing 802. In this regard, the consumable housing 810 includes a cutout or voided portion 814 that corresponds to the peristaltic pump mechanism 820, such that the rotor 819 of the peristaltic pump mechanism 820 extends into the cutout portion 814 of the consumable housing 810 to engage a fluid conduit 821 (or tubing) provided therein when the consumable 806 is inserted into the cutout portion 804 of the infusion device housing 802. In this regard, the infusion device 800 includes a rotary shaft 817 extending from the infusion device housing 802 into the cutout portions 804, 814, with the shaft 817 being coupled to the rotor 819. The rotor 819 includes rollers 816 of the peristaltic pump mechanism 820 that are coupled thereto, and the rollers 816 compress the tubing 821 housed within the cutout portion 814 of the consumable housing 810 when the consumable 806 and the infusion device 800 are engaged. As the rollers 816 compress and traverse the tubing 821 in response to rotation of the rotor 819 and shaft 817, fluid is drawn into the tubing 821 from the reservoir 108 and dispensed downstream via the infusion arrangement 822.

As described above, the consumable 806 may be calibrated in accordance with the calibration process 300 of FIG. 3 prior to mating or engaging the consumable 806 with the infusion device housing 802. The infusion device housing 802 includes an interface 118 configured to access a readable element 124 contained within or physically associated with the consumable housing 810, to read or otherwise retrieve the configuration data associated with the consumable 806 and then operate the peristaltic pump mechanism 120, 820 in accordance with the configuration data in a similar manner as described above in the context of the control process 200 of FIG. 2. Thus, the calibration data associated with the consumable 806 accounts for variations in the dimensions of the tubing 821 (e.g., the inner diameter) and/or potentially other fluid path components of the consumable 806, thereby allowing the control module 112 of the infusion device 102, 400 to adjust actuation or operation of the actuation components 116, 117, 119, 817 to adapt to the current instance of the consumable 806 and achieve a desired dosage of fluid delivery as described above.

Again, it should be noted that in practice there are numerous different types of pumping mechanisms which may be utilized with an infusion device, and numerous different types of integration or packaging schemes which may be utilized to distribute actuation of the pumping mechanism across one or more of the infusion device and the consumable. Accordingly, the subject matter described herein is not intended to be limited to any particular type of pumping mechanism, nor any particular manner of implementing or integrating the pumping mechanism with either of the infusion device or the consumable. Regardless of the particular implementation, the control process 200 of FIG. 2 and the calibration process 300 of FIG. 3 may be performed to adaptively control operations of the infusion device to deliver fluid in a manner that accounts for variations in the dimensions or other physical characteristics of the various instances of a consumable that may be utilized with the infusion device.

Figure 10:
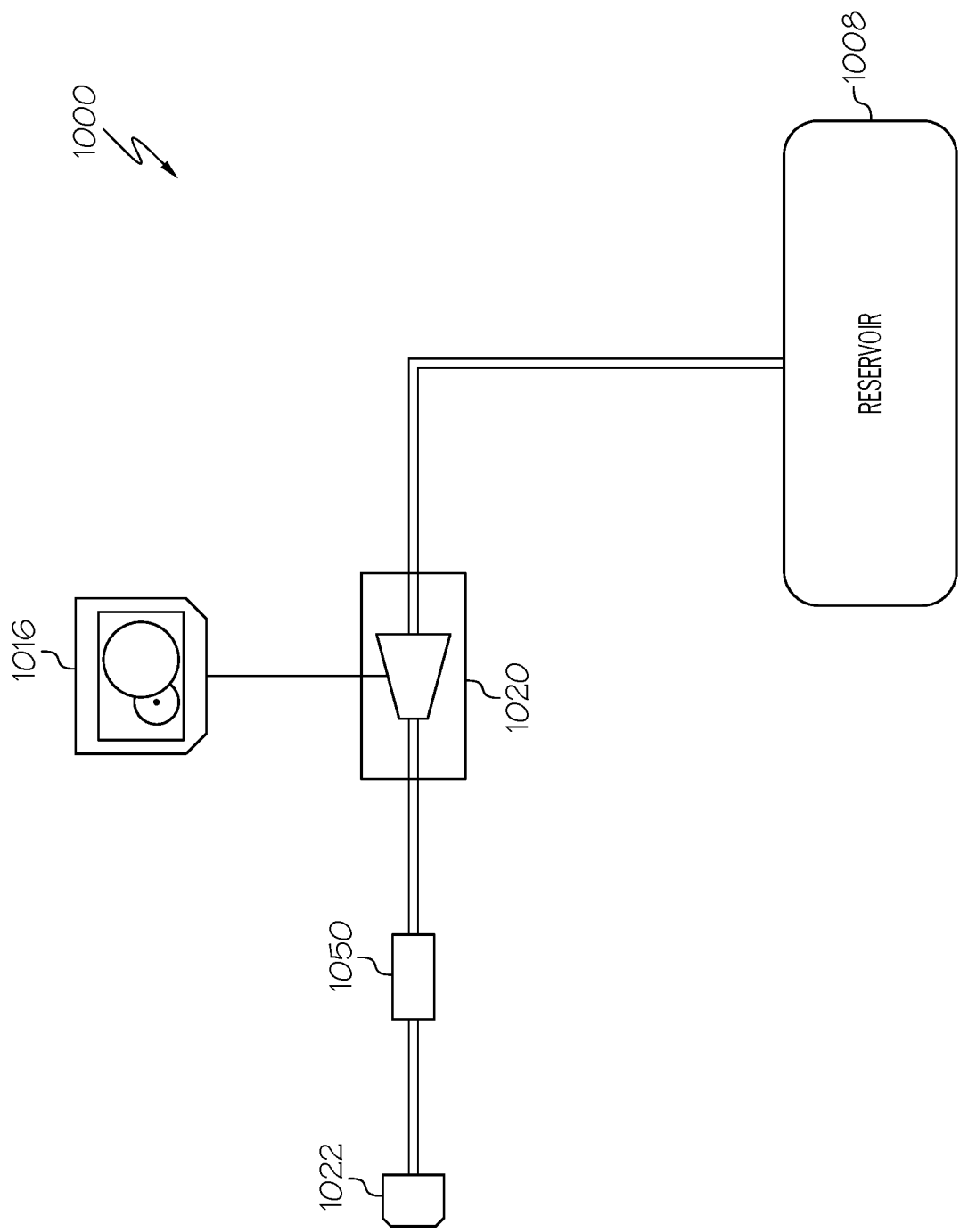
FIG. 10 depicts an exemplary embodiment of a fluid delivery system suitable for implementation in the infusion system of FIG. 1 in conjunction with the control process of FIG. 2 and the calibration process of FIG. 3 in accordance with one or more embodiments.

FIG. 10 depicts a simplified representation of a fluid delivery system 1000 suitable for implementation in an infusion system 100 and usage in conjunction with the processes 200, 300 described above. The fluid delivery system 1000 includes a pumping mechanism 1020 arranged between a reservoir 1008 and an output interface 1022 to an infusion set to pump, deliver, or otherwise dispense fluid from the reservoir 1008 to a body of a user via the infusion set in response to operation or actuation of a drive system 1016. In this regard, the drive system 1016 may include one or more motors or other actuators, gear reducers or other gearing or transmission components, and the like. In exemplary embodiments, the reservoir 1008 and the pumping mechanism 1020 are integrated or otherwise embodied in a consumable that engages with an infusion device, which includes an instance of the drive system 1016, as described above.

As described above in the context of FIG. 3, the embodiment of FIG. 10 includes a sensing arrangement 1050 configured to measure a fluid response to actuation of the drive system 1016, and thereby calibrate or otherwise characterize the relationship between actuation of a drive system 1016 and the rate or amount of fluid delivered by the instance of the consumable including the pumping mechanism 1020 being calibrated. The sensing arrangement 1050 could be realized as a flow meter or volume sensor, a pressure sensor, or another suitable sensor capable of quantifying a fluid response. In the illustrated embodiment, the sensing arrangement 1050 is provided downstream of the pumping mechanism 1020, and in some embodiments, the sensing arrangement 1050 is provided downstream of the output interface 1022 to obtain a measured response that accounts for variations associated with the pumping mechanism 1020, the output interface 1022, and any tubing or other components that may be part of the fluid path from the reservoir 1008 to the output interface 1022. The sensing arrangement 1050 is also capable of being detachably or selectively coupled to the downstream fluid path, so that the sensing arrangement 1050 can be disengaged from a consumable once it is calibrated and subsequently reused to calibrate other instances of the consumable. Similarly, a reference drive system 1016 may be disengaged or decoupled from the consumable once it is calibrated and subsequently reused to calibrate other instances of the consumable.

In alternative embodiments, the sensing arrangement 1050 (or an additional second sensing arrangement) may be provided upstream of the pumping mechanism 1020 but downstream of the reservoir 1008. In embodiments where multiple sensing arrangements 1050 are employed both upstream and downstream of the pumping mechanism 1020, the measured responses obtained from the different sensing arrangements 1050 may be averaged or otherwise combined to obtain an average measured response to actuation of the pumping mechanism 1020. It should be noted that a sensing arrangement upstream of the pumping mechanism 1020 may be utilized to detect depletion of the reservoir 1008 during calibration (e.g., when to cease actuating the drive system 1016 and/or obtaining measured responses), while a sensing arrangement downstream of the pumping mechanism 1020 may be utilized to detect an occlusion in the fluid path. In some embodiments, a consumable may be discarded in response to detection of a fluid path occlusion when the occlusion cannot be remediated or removed.

It should be noted that the type of sensing arrangement 1050 employed during manufacturing for calibration purposes may be different from sensing arrangements that may be part of the consumable or the infusion device and used during subsequent operation. For example, the sensing arrangement 1050 may be realized as a relatively high sensitivity pressure sensor that measures pressure response to actuation of the pumping mechanism 1020 to determine a corresponding amount of fluid delivered per unit of actuation of the pumping mechanism 1020 (e.g., a calibrated stroke volume of a piston pumping mechanism). Thereafter, the consumable or infusion device may be equipped with or otherwise employ a force sensor, an optical sensor, or the like that is then used during operation to detect occlusion conditions, reservoir depletion, or other conditions that may be exhibited by the consumable during operation of the infusion device. In this regard, by virtue of the calibration described herein, the consumable does not necessarily need to be equipped with a flow meter or other sensors for measuring fluid delivery.

During or after the manufacturing of the consumable including the pumping mechanism 1020 and reservoir 1008, a reference instance of the drive system 1016 is operated to actuate the pumping mechanism 1020 by some reference amount, and a corresponding fluid response is measured, quantified, or otherwise obtained via the sensing arrangement 1050. Based on the relationship between the measured fluid response and the actuation of the drive system 1016 and/or pumping mechanism 1020, the calibration data associated with the consumable characterizing the relationship between actuation of the pumping mechanism 1020 and the resulting fluid delivery is determined.

After calibration data associated with the consumable is determined, the calibration data written to or otherwise stored on a readable element associated with the consumable. For example, a control module, a processing system, or the like, may be coupled to drive system 1016 to provide the reference amount of actuation, coupled to the sensing arrangement 1050 to receive the measured fluid response, and coupled the readable element to write or otherwise store calibration data to the readable element, which was calculated or otherwise determined by the control module based on the relationship between the reference amount of actuation and the measured fluid response. In some embodiments, physical measurements of aspects of the pumping mechanism 1020 and/or other fluid path components are obtained (e.g., using an optical measuring device, a touch probe measuring device, or the like) and the corresponding measurement data also written to or otherwise stored on a readable element associated with the consumable.

In some embodiments, the pumping mechanism 1020 may be calibrated during manufacturing and prior to assembly in the consumable. For example, the pumping mechanism 1020 may be calibrated without the presence of a fluid reservoir 1008 (e.g., using air) or with a reference instance of the reservoir 1008 that is different from the reservoir 1008 that is ultimately packaged with the pumping mechanism 1020 in the consumable. In this regard, an instance of a fluid reservoir 1008 may be provided or otherwise packaged within a housing of the consumable, and then after calibration of an instance of the pumping mechanism 1020, that instance of the pumping mechanism 1020 may be provided or otherwise packaged within the housing and configured so that the pumping mechanism 1020 is in fluid communication with the reservoir 1008 to thereby provide a path for fluid flow from the reservoir 1008 via the pumping mechanism 1020. In one embodiment, a barcode representation of the calibration data is printed or otherwise provided on an external surface of the housing of the consumable. In another embodiment, the calibration data is written to or otherwise stored on a RFID tag, which may be packaged or contained within the housing of the consumable or integrated with an external surface of the housing. In another embodiment, the calibration data is written to or otherwise stored on a data storage element that is packaged or contained within the housing. Depending on the embodiment, the readable element may be configured or packaged with the consumable housing either before or after packaging the pumping mechanism 1020 and/or the reservoir 1008 within the consumable housing.

After manufacturing, the consumable may be engaged with an infusion device which is configured to read the calibration data, measurement data, and/or other configuration data that was written to the readable element and adjust actuation of its associated drive system 1016 in a manner that accounts for variations in the dimensions or other physical characteristics of the pumping mechanism 1020 and other fluid path components of the consumable currently being utilized with the infusion device. In this manner, actuation of the pumping mechanism 1020 is corrected or adjusted to achieve a desired delivery of fluid with greater precision across different consumables. In particular, some embodiments may utilize the calibration data in conjunction with the physical measurement data to fine tune the actuation, for example, by adjusting actuation commands based on a function of the calibration data for the fluid response to actuation of the pumping mechanism 1020 and the dimensions or other physical measurements of the pumping mechanism 1020. Since fluid volume accuracy may be a function of dimensions of the pumping mechanism 1020 (which are captured by the measurement data) as well as the mechanics of the pumping mechanism 1020 (which are captured by the calibration data), adjusting actuation based on configuration data that includes both fluid response calibration data and physical measurement data may improve accuracy and reliability across a wide range of consumables and across a wide range of delivery or dosage amounts (or rates).

While the subject matter is described above primarily in the context of a consumable containing an insulin reservoir for regulating a glucose level of a user, the subject matter described herein is not limited to any type of media dispensed from or otherwise provided by the consumable, and the subject matter may be implemented with other medical devices or electronic devices other than fluid infusion devices. For example, any electronic device could be configured to receive a consumable component and consume or deliver a medium from the consumable component, where the housing of the consumable component includes a readable element provided on, integrated with, or otherwise physically associated therewith that includes calibration data characterizing a relationship between depletion of the medium and actuation of an actuatable mechanism engaged therewith, thereby enabling a control module or processing system of the device to adaptively control the actuation of the actuatable mechanism in accordance with the configuration data.

For the sake of brevity, conventional techniques related to glucose sensing and/or monitoring, closed-loop glucose control, sensor calibration, electrical signals and related processing, electrical interconnects or interfaces, packaging, fluid communications, fluid monitoring or measuring, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of manufacturing a consumable component, the method comprising:
    actuating, by a control module, a pumping mechanism of the consumable component by a reference amount, the consumable component comprising a housing containing a reservoir, the pumping mechanism for dispensing a fluid from the reservoir and a readable element associated with the housing, the pumping mechanism including a mechanism for translating rotation to a linear displacement of a piston coupled to the mechanism;
    obtaining, by the control module from a sensing arrangement, a measured response to the reference amount;
    determining, by the control module, calibration data associated with the consumable component characterizing a relationship between delivery of the fluid and actuation of the pumping mechanism based on the relationship between the measured response and the reference amount; and
    writing, by the control module, the calibration data associated with the consumable component to the readable element.

2. The method of claim 1, wherein writing the calibration data comprises providing a barcode representation of the calibration data on a housing of the consumable component.

3. The method of claim 1, wherein writing the calibration data comprises writing the calibration data to a radio frequency identification (RFID) tag contained within a housing of the consumable component.

4. The method of claim 1, wherein writing the calibration data comprises storing the calibration data on a data storage element contained within a housing of the consumable component.

5. The method of claim 1, wherein obtaining the measured response comprises obtaining a measured volume of fluid from a flow meter downstream of the pumping mechanism.

6. The method of claim 1, wherein obtaining the measured response comprises obtaining a measured pressure from a pressure sensor downstream of the pumping mechanism.

7. The method of claim 6, wherein determining the calibration data comprises:
    converting the measured pressure to a corresponding amount of fluid delivery; and
    determining a calibration factor based on a relationship between the reference amount of actuation and the corresponding amount of fluid delivery.

8. The method of claim 1, further comprising:
    providing the reservoir containing the fluid within the housing of the consumable component; and
    providing the pumping mechanism within the housing of the consumable component after actuating the pumping mechanism by the reference amount and obtaining the measured response, wherein the pumping mechanism is in fluid communication with the reservoir.

9. The method of claim 8, further comprising providing the readable element on a surface of the housing of the consumable component after determining the calibration data.

* * * * *